(12) United States Patent
Eberwine et al.

(10) Patent No.: US 9,547,007 B2
(45) Date of Patent: Jan. 17, 2017

(54) METHODS AND COMPOSITIONS FOR IN-VIVO ENZYME CAPTURE

(75) Inventors: James Eberwine, Philadelphia, PA (US); Ülo Langel, Stockholm (SE); Emelia Eiriksdóttir, Reyjavik (IS); Anup Sharma, Philadelphia, PA (US)

(73) Assignee: The Trustees of the University of Pennslyvania, Philadelphia, PA (US)

( * ) Notice: Subject to any disclaimer, the term of this patent is extended or adjusted under 35 U.S.C. 154(b) by 0 days.

(21) Appl. No.: 13/395,362

(22) PCT Filed: Sep. 22, 2010

(86) PCT No.: PCT/US2010/049826
§ 371 (c)(1),
(2), (4) Date: Oct. 22, 2012

(87) PCT Pub. No.: WO2011/038004
PCT Pub. Date: Mar. 31, 2011

(65) Prior Publication Data
US 2013/0040309 A1  Feb. 14, 2013

Related U.S. Application Data

(60) Provisional application No. 61/244,815, filed on Sep. 22, 2009.

(51) Int. Cl.
*G01N 33/573*  (2006.01)
*C07K 19/00*  (2006.01)

(52) U.S. Cl.
CPC .................. *G01N 33/573* (2013.01)

(58) Field of Classification Search
CPC .................................................. G01N 33/573
See application file for complete search history.

(56) References Cited

U.S. PATENT DOCUMENTS

| 5,188,934 | A | 2/1993 | Menchen et al. |
| 5,366,860 | A | 11/1994 | Bergot et al. |
| 6,025,140 | A | 2/2000 | Langel et al. |
| 6,180,370 | B1 | 1/2001 | Queen et al. |
| 6,238,667 | B1 * | 5/2001 | Kohler ............. C07K 14/472 424/178.1 |
| 2008/0199854 | A1 * | 8/2008 | Eberwine et al. ........ 435/6 |
| 2008/0274962 | A1 | 11/2008 | Shoshan-Barmatz et al. |

FOREIGN PATENT DOCUMENTS

WO  WO 87/02671  5/1987

OTHER PUBLICATIONS

Sigma-Aldrich, "Antibodies to Biotin," accessed Oct. 30, 2013.*
Krypides et al. (J. Mol Evol, (1985) vol. 40: 564-569).*
Shen et al. ("Modulation of nuclear internalization of Tat peptides by fluorescent dyes and receptor-avid peptides" FEBS Lett. May 2007; 581:1793-1799.*
Altschul et al., "Gapped BLAST and PSI-BLAST: a new generation of protein database search programs." 1997, Nucleic Acids Res. 25:3389-3402.
Altschul, et al., "Basic local alignment search tool." 1990, J. Mol. Biol. 215:403-410.
Braslawsky et al., "Adriamycin(hydrazone)-antibody conjugates require internalization and intracellular acid hydrolysis for antitumor activity." 1991, Cancer Immunol Immunother. 33:367-74.
Cardullo et al., "Detection of nucleic acid hybridization by nonradiative fluorescence resonance energy transfer," 1988, Proc Nati Acad Sci U S A. 85:8790-8794.
Clegg, "Fluorescence resonance energy transfer and nucleic acids." 1992, Meth. Enzymol. 211:353 388.
Derossi et al., "The third helix of the Antennapedia homeodomain translocates through biological membranes." 1994, J Biol Chem 269:10444-10450.
Eiriksdottir et al., "Cellular Uptake of Cell-Penetrating Peptides," 2004, Drug Delivery Reviews-Online 1(2):161-173.
Fletcher et al., "Facile preparation of an orthogonally protected, pH-sensitive, bioconjugate linker for therapeutic applications." 2004, Org Lett. 6:4245-4248.
Grether et al., "An enzyme-labile safety catch linker for synthesis on a soluble polymeric support." 2001, Chemistry 7:959-971.
Gu et al., "Construction and expression of mouse-human chimeric antibody SZ-51 specific for activated platelet P-selectin." 1997, Thrombosis and Haemostasis 77(4):755-759.
Habert-Ortoli et al., "Molecular cloning of a functional human galanin receptor." 1994, Proc. Natl. Acad. Sci. USA, 91:9780-83.
Hallbrink et al., "Cargo delivery kinetics of cell-penetrating peptides." 2001, Biochim Biophys Acta. 1515:101-9.
Karlin and Altschul, "Methods for assessing the statistical significance of molecular sequence features by using general scoring schemes." 1990, Proc, Natl. Acad. Sci. USA 87:2264-2268.
Karlin and Altschul, "Applications and statistics for multiple high-scoring segments in molecular sequences." 1993, Proc. Natl. Acad. Sci. USA 90:5873-5877.
Pooga et al., "Synthesis of cell-penetrating peptide-PNA constructs." 2002, Methods Mol. Biol. 208:225-36.
Pooga, M., et al.,"Cellular translocation of proteins by transportan." 2001, FASEB J., 10:1096.
Pooga, M., et al., "Cell penetration by transportan." 1998, FASEB J., 12:67-77.
Pooga, M., et al., "Cell penetrating PNA constructs regulate galanin receptor levels and modify pain transmission in vivo." 1998, Nat. Biotechnol., 16:857-61.
Vives et al., 1997, "A truncated HIV-1 Tat protein basic domain rapidly translocates through the plasma membrane and accumulates in the cell nucleus." J Biol Chem 272:16010-16017.
Wright et al., "Genetically engineered antibodies: progress and prospects." 1992, Critical Rev. Immunol. 12:125-168.

* cited by examiner

*Primary Examiner* — James H Alstrum Acevedo
*Assistant Examiner* — Tara Martinez
(74) *Attorney, Agent, or Firm* — Riverside Law LLP

(57) ABSTRACT

The invention includes compositions, methods and kits for the in vivo identification of an enzyme that binds to a substrate. The invention comprises, in part, a photoreactive moiety to aid in identification of such an enzyme.

2 Claims, 4 Drawing Sheets

SEQUENCE LISTING

```
<160> NUMBER OF SEQ ID NOS: 5

<210> SEQ ID NO 1
<211> LENGTH: 21
<212> TYPE: PRT
<213> ORGANISM: artificial
<220> FEATURE:
<223> OTHER INFORMATION: Synthetic Construct

<400> SEQUENCE: 1

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 2
<211> LENGTH: 27
<212> TYPE: PRT
<213> ORGANISM: artificial
<220> FEATURE:
<223> OTHER INFORMATION: Synthetic Construct
```

-continued

```
<400> SEQUENCE: 2

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 3
<211> LENGTH: 16
<212> TYPE: PRT
<213> ORGANISM: artificial
<220> FEATURE:
<223> OTHER INFORMATION: Synthetic Construct

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 13
<212> TYPE: PRT
<213> ORGANISM: artificial
<220> FEATURE:
<223> OTHER INFORMATION: Synthetic Construct

<400> SEQUENCE: 4

Gly Arg Lys Lys Arg Arg Gln Arg Arg Arg Pro Pro Gln
1               5                   10

<210> SEQ ID NO 5
<211> LENGTH: 10
<212> TYPE: PRT
<213> ORGANISM: artificial
<220> FEATURE:
<223> OTHER INFORMATION: Synthetic Construct

<400> SEQUENCE: 5

Glu Gln Lys Leu Ile Ser Glu Glu Asp Leu
1               5                   10
```

US 9,547,007 B2

METHODS AND COMPOSITIONS FOR IN-VIVO ENZYME CAPTURE

CROSS-REFERENCE TO RELATED APPLICATIONS

This application is the U.S. national phase application filed under 35 U.S.C. §371 claiming benefit to International Patent Application No. PCT/US10/49826, filed on Sep. 22, 2010, which is entitled to priority under 35 U.S.C. §119(e) to U.S. Provisional Patent Application No. 61/244,815, filed on Sep. 22, 2009, each of which application is hereby incorporated herein by reference in its entirety.

BACKGROUND OF THE INVENTION

Enzyme-substrate interactions play a critical role in a variety of biochemical processes. For example, these interactions play a role in the extracellular and intracellular signaling events and in the transcriptional and translational control of gene expression. Abnormal or disease states can be the direct result of abnormal enzyme-substrate interactions. Identification of specific enzyme-substrate complexes will enable the development of tools useful in the regulation of cell signaling and gene expression. This in turn will enable the biological manipulation of cell signaling and gene expression in the laboratory, as well as the development of therapeutic tools for manipulating cellular processes.

Enzyme-substrate interactions have been studied using both biochemical and genetic methods to gain understanding about enzyme-substrate binding activity and to identify unknown enzyme binding partners. These methods include coimmunoprecipitation, pull-down, chemical crosslinking, label transfer, tandem affinity purification (TAP), and two-hybrid assays (see Golemis, 2002, Protein-protein Interactions: A Molecular Cloning Manual, Cold Spring Harbor Laboratory and Fu, 2004, Protein-protein Interactions: Methods and Applications, Humana Press). The utility and applicability of the results obtained using these standard methods is limited with respect to obtaining a detailed understanding of enzyme-substrate binding activity, since the methods reveal which binding interactions occur in vitro or in an otherwise artificial environment. To truly understand the dynamics of enzyme-substrate interactions, it is first necessary to possess the ability to identify the interactions in vivo.

What is needed is a methodology that provides for the identification of enzymes that interact in vivo with a target substrate. Therefore, there exists a long felt need to provide a way to identify enzymes that interact with a pre-selected substrate in vivo. The present invention addresses and meets this need.

BRIEF SUMMARY OF THE INVENTION

The invention features a membrane-permeable construct for transport of the construct across a lipid membrane. In one embodiment, the membrane-permeable construct of the invention includes a substrate moiety, which interacts with an intracellular enzyme. In one embodiment, the substrate moiety includes at least one photoreactive moiety. In one embodiment, the membrane-permeable construct of the invention includes a peptide moiety, comprising $R_1$-CPP-$R_2$, wherein CPP is a cell-penetrating peptide, and further wherein each of $R_1$ and $R_2$ are independently selected from the group consisting of a peptide, an amino acid, $NH_2$, H, or OH, and further wherein the substrate moiety is covalently attached to one of the members selected from the group consisting of $R_1$, $R_2$, a cysteine residue within the peptide moiety, or a lysine (K) residue within the peptide moiety. In one embodiment, the membrane-permeable construct of the invention also includes a chemical bond linking the substrate moiety and the peptide moiety.

In various embodiments, the CPP of the membrane-permeable construct of the invention is at least one of: SEQ ID NO:1, SEQ ID NO:2, SEQ ID NO:3, and SEQ ID NO:4. In one embodiment, the chemical bond linking the substrate moiety and the peptide moiety is labile. In various embodiments, the labile chemical bond is at least one of: a disulfide bond, an ester bond, an avidin-biotin linkage, a cyclic unsaturated maleamate, and a 13-acylhydrazone. In one embodiment, at least one of $R_1$ and $R_2$ is a cysteine, and the substrate moiety is disulfide bonded to the cysteine. In one embodiment, the peptide moiety of the membrane-permeable construct is a homolog or a conservative variant of SEQ ID NO:1.

In various embodiments, the substrate moiety of the membrane-permeable construct of the invention is at least one of: a peptide sequence identified as a putative site of interaction with a known enzyme; a peptide sequence suspected to be a putative site of interaction with a known enzyme; a peptide sequence identified as a putative site of interaction with an unknown enzyme; a peptide sequence suspected to be a putative site of interaction with a unknown enzyme; a peptide sequence comprising a known post-translational modification site; a peptide sequence comprising a known chemical modification site; a peptide sequence comprising a known feature associated with an enzyme-substrate interaction; a peptide sequence comprising a unknown post-translational modification site; a peptide sequence comprising a unknown chemical modification site; and a peptide sequence comprising a unknown feature associated with an enzyme-substrate interaction.

In various embodiments, the photoreactive moiety of the membrane-permeable construct of the invention is at least one of: a photoreactive amino acid, a p-benzoylbenzoyl (BzBz) moiety, an azide moiety, a 4-benzoylbenzoic acid derivative, a 4-azido-2,3,5,6,-tetrafluorobenzoic acid derivative, and an N-((2-pyridyldithio)ethyl)-4-azidosalicylamide derivative. In various embodiments, the photoreactive moiety of the membrane-permeable construct of the invention is at least one of: para-benzoyl-L-phenylalanine (Bpa) and para-azido-L-phenylalanine (Apa).

In one embodiment the membrane-permeable construct of the invention further includes a label. In various embodiments, the label of the membrane-permeable construct of the invention is at least one of: biotin, dinitrophenyl, acridine, fluorescein, rhodamine, cyanine, digoxigenin, a chemiluminescent precursor, selenium and cadmium. In one embodiment, the label of the membrane-permeable construct of the invention is a known-antibody epitope.

In one embodiment, the substrate moiety of the membrane-permeable construct of the invention is joined to a lysine residue in the peptide moiety through a disulfide bond. In various embodiments of the membrane-permeable construct of the invention, the C-terminal leucine residue is at least one selected from the group consisting of: amidated and left as an acid. In one embodiment, the disulfide bond of the membrane-permeable construct of invention is disposed between a pair of cysteine residues.

The invention also features a membrane-permeable construct for transport of the construct across a lipid membrane that includes a substrate moiety of the structure $R_3$-Cys-SUBSTRATE-Lys-amide which interacts with an intracellular enzyme, wherein $R_3$ is a photoreactive amino acid. In one embodiment, the construct also includes a peptide moiety comprising $R_1$-AGYLLGKINLKALAALAKKIL-$R_2$ (SEQ ID NO:1), wherein $R_1$ is hydrogen and $R_2$ is $NH_2$, further wherein the substrate moiety is covalently attached to a cysteine residue within the peptide moiety. In one embodiment, the construct also includes a disulfide bond linking the substrate moiety and the peptide. In another embodiment, the substrate moiety of the construct of the invention has the structure Bpa-Cys-SUBSTRATE-Lys-amide.

In various embodiments, the substrate moiety of the construct of the invention is at least one selected from the group consisting of: a peptide sequence identified as a putative site of interaction with a known enzyme; a peptide sequence suspected to be a putative site of interaction with a known enzyme; a peptide sequence identified as a putative site of interaction with an unknown enzyme; a peptide sequence suspected to be a putative site of interaction with a unknown enzyme; a peptide sequence comprising a known post-translational modification site; a peptide sequence comprising a known chemical modification site; a peptide sequence comprising a known feature associated with an enzyme-substrate interaction; a peptide sequence comprising a unknown post-translational modification site; a peptide sequence comprising a unknown chemical modification site; and a peptide sequence comprising a unknown feature associated with an enzyme-substrate interaction.

The invention also features methods of identifying an enzyme that interacts with a substrate. In one embodiment, the method of the invention includes the steps of: a) providing a membrane permeable construct for transport of the construct across a lipid membrane comprising: i) a substrate moiety which interacts with an intracellular enzyme, the substrate moiety comprising at least one photoreactive moiety; ii) a peptide moiety comprising $R_1$-CPP-$R_2$, wherein CPP is a cell-penetrating peptide, further wherein each of $R_1$ and $R_2$ are independently selected from the group consisting of a peptide, an amino acid, $NH_2$, H, or OH, further wherein the substrate moiety is covalently attached to one of the members selected from the group consisting of $R_1$, $R_2$, a cysteine residue within the peptide moiety, or a lysine (K) residue within the peptide moiety; and iii) a chemical bond linking the substrate moiety and the peptide moiety; b) allowing the construct to interact with the intracellular enzyme to form a construct-enzyme complex, under conditions suitable for binding of the construct with the enzyme; c) activating the photoreactive moiety, thereby covalently cross-linking the substrate moiety with the enzyme that interacts with the substrate; d) isolating the crosslinked substrate-enzyme from the cell; and e) identifying the enzyme crosslinked to the substrate; thereby identifying an enzyme that interacts with a substrate.

In one embodiment, the method includes an isolation step d) wherein i) lysing the cell containing the crosslinked substrate-enzyme to form a cell lysate; ii) contacting the cell lysate with a solid support comprising an antibody specific for at least one of the members of the group consisting of: A) the CPP; B) the substrate moiety; and C) the CPP-substrate moiety construct; under conditions suitable to allow the crosslinked substrate-enzyme to bind to the antibody to form a complex; and iii) separating the complex from the lysate.

The invention also features kits for the identification of an enzyme that interacts with a substrate. In one embodiment, the kit of the invention includes a membrane permeable construct for transport of the construct across a lipid membrane, which includes a substrate moiety which interacts with an intracellular enzyme, the substrate moiety comprising at least one photoreactive moiety; a CPP moiety comprising $R_1$-CPP-$R_2$, wherein CPP is a cell-penetrating peptide, further wherein each of $R_1$ and $R_2$ are independently selected from the group consisting of a peptide, an amino acid, $NH_2$, H, or OH, further wherein the substrate moiety is covalently attached to one of the members selected from the group consisting of $R_1$, $R_2$, a cysteine residue within the CPP moiety, or a lysine (K) residue within the CPP moiety; and a chemical bond linking the substrate moiety and the CPP moiety. In some embodiments, the kit of the invention further includes and an applicator and instructional material for the use of the kit.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
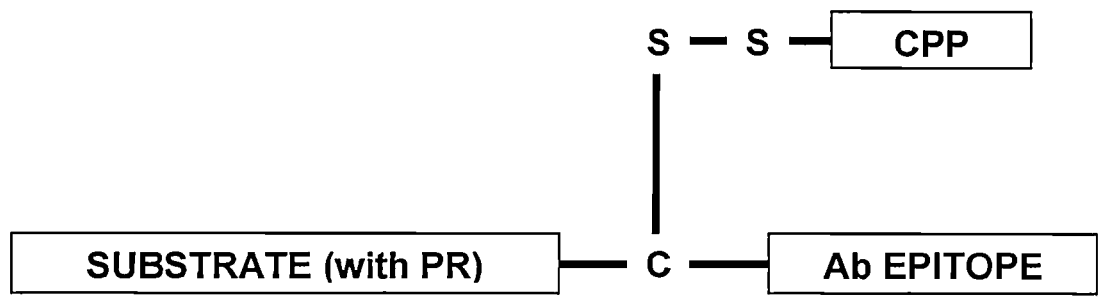
FIG. 1 depicts an example construct comprising a cell penetrating peptide (CPP) moiety linked to a substrate moiety that contains a photoreactive moiety (PR). The example construct also includes an optional known-antibody epitope to facilitate the isolation of the construct and identification of cross-linked enzymes. The figure is not drawn to scale.
Figure 2:
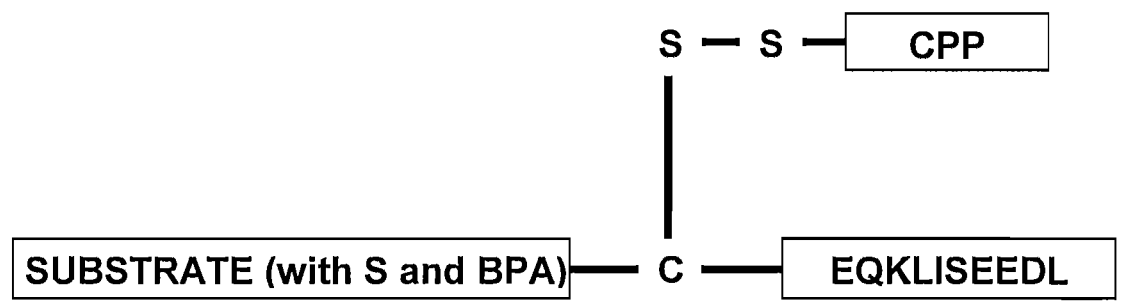
FIG. 2 depicts an example construct for capturing a kinase targeting a serine site (S) and surrounding sequence of a substrate-of-interest. In place of one of the amino acids, a photoreactive amino acid analog is synthesized into the substrate-of-interest sequence (i.e., BPA). This substrate sequence is depicted coupled via a cysteine linker to a another peptide sequence corresponding to a known-antibody epitope (i.e., c-myc peptide) to facilitate the isolation (for example, by using immunoprecipation) of the construct and any cross-linked enzymes. A CPP is coupled to the linker cysteine via disulfide bond. The figure is not drawn to scale.
Figure 3:
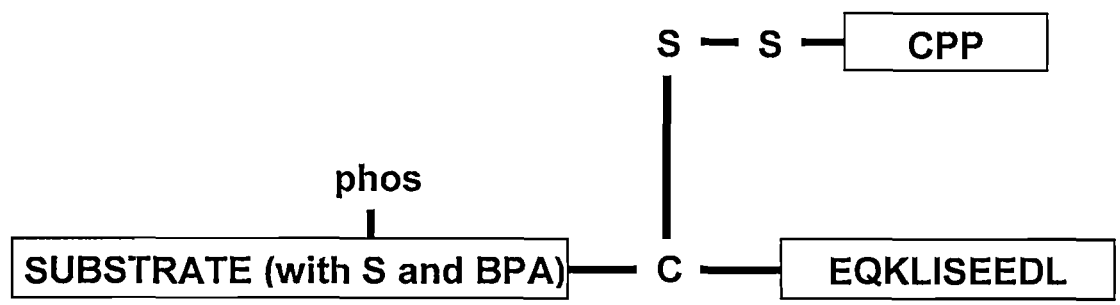
FIG. 3 depicts an example construct for capturing a phosphatase targeting a phosphorylated serine site (S-phos) and surrounding sequence of a substrate-of-interest. In place of one of the amino acids, a photoreactive amino acid analog is synthesized into the substrate-of-interest sequence (i.e., BPA). This substrate sequence is depicted coupled via a cysteine linker to a another peptide sequence corresponding to a known-antibody epitope (i.e., c-myc peptide) to facilitate the isolation (for example, by using immunoprecipitation) of the construct and any cross-linked enzymes. A CPP is coupled to the linker cysteine via disulfide bond. The figure is not drawn to scale.

The present invention provides compositions and methods for the in vivo identification of enzymes, such as, for example, kinases and phosphatases. Through the combination of a cell penetrating peptide (CPP) and a substrate moiety containing a photoreactive amino acid analog, such as benzoyl-phenylalanine (BpA), the present invention provides, for the first time, methods and compositions for the identification of enzymes that interact in vivo with a target substrate. The present invention provides a CPP-substrate moiety construct, further including a photoreactive label, that can be used to target, crosslink and identify the enzymes that bind to a particular substrate moiety in vivo, through targeted cross-linking of the CPP-substrate construct with the intracellular enzyme. Optionally, the construct further comprises a known-antibody epitope to facilitate the isolation of the construct and any cross-linked enzymes. Additionally, the compositions and methods of the present invention can be extended to the use of other known substrates.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

"Amplification" refers to any means by which a polynucleotide sequence is copied and thus expanded into a larger number of polynucleotide molecules, e.g., by reverse transcription, polymerase chain reaction, and ligase chain reaction, among other methods.

The term "antibody" as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Antisense" refers to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, and the like, for administering one or more molecules such as, but not limited to, a nucleic acid, a protein, and a small-molecule chemical moiety to a mammal.

"Binding" is used herein to mean that a first moiety physically interacts with a second moiety, wherein the first and second moieties are in physical contact with one another.

"Biological sample," as that term is used herein, means a sample obtained from or in a mammal that can be used to assess the level of expression of a nucleic acid, the level of a protein present, or both. Such a sample includes, but is not limited to, a cell, a blood sample, a neural tissue sample, a brain sample, and a cerebrospinal fluid sample.

A "cell penetrating peptide" is used herein to refer a polypeptide that facilitates the entry of said polypeptide, along with any molecule associated with the polypeptide, across one or more membranes to the interior of a cell.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A first region of an oligonucleotide (or polypeptide), "flanks" a second region of the oligonucleotide (or polypeptide), if the two regions are adjacent one another or if the two regions are separated by no more than about 1000 nucleotide residues, and preferably no more than about 100 nucleotide residues.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is naturally-occurring.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cisacting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

"Conjugate" or "conjugated" refer to a covalent, ionic, or hydrophobic interaction whereby the moieties of a molecule are held together and preserved in proximity.

"Linker" refers to one or more atoms comprising a chain connecting a substrate moiety to a moiety such as a peptide, label, modifier, stabilizing group, or the like.

"Chimera" as used herein refers to a substrate moiety including one or more peptide units.

"Phosphodiester analog" or "internucleotide analog" refer to analogs of natural phosphodiester 3',5'-internucleotide linkages differing in their composition and/or location of attachment to a nucleotide, including but not limited to 2',5'-linkage, 3',3'-linkage, 5',5' linkage, methyl phosphonate, alkylated phosphotriester, 3'-N-phosphoramidate, and non-bridging N-substituted phosphoramidate.

The term "2'-modified RNA" means a polynucleotide containing one or more ribonucleotides in which a 2' position on a sugar bears a substituent replacing a hydroxyl. As an example, 2'-O-alkyl RNA comprises a polynucleotide containing one or more ribonucleotides in which a 2' position on a sugar consists of the moiety —OR where R is lower alkyl, such as, but not limited to, a methyl or ethyl moiety (Sproat, 1994, Protocols for Oligonucleotides and Analogs, Humana Press).

The terms "permeant" and "permeable" refer to the ability of a construct of the present invention to pass through a cellular membrane, or ascribed as characteristics of the susceptibility of cellular membranes to have constructs pass through them (Alberts et al., 1989, Molecular Biology of the Cell, 2nd Ed., Garland Publishing, New York).

"Label" refers to a group covalently attached to some portion of the CPP-substrate construct. The label is capable of conducting a function such as giving a signal for detection of the molecule by such means as fluorescence, chemiluminescence, and electrochemical luminescence. Alternatively, the label allows for separation or immobilization of the molecule by a specific or non-specific capture method (Andrus, 1995, PCR 2: A Practical Approach, Oxford University Press, Oxford, pp. 39-54), such as, for example, a known-antibody epitope. Labels include, but are not limited to, photoreactive labels, fluorescent dyes, such as fluorescein and rhodamine derivatives (Menchen et al., 1993, U.S. Pat. No. 5,188,934; Bergot et al., 1994, U.S. Pat. No. 5,366,860), cyanine dyes, and energy-transfer dyes (Clegg, 1992, Meth. Enzymol. 211:353-388; Cardullo et al., 1988, PNAS 85:8790-8794).

A "photoreactive label" refers to a label that becomes chemically active upon irradiation of the label with light energy. Light energy useful for activating such labels includes, but is not limited to, visible light, ultraviolet (UV) light, infrared (IR) light, among others. An activated label may contain a free radical, or other highly reactive group, and may be reactive with an adjacent molecule. By way of a non-limiting example, parabenzoylphenylalanine (BPA) is a photoreactive amino acid that may be incorporated into a peptide. Activation of BPA with UV light causes the benzoyl moiety of the amino acid to be released, leaving a phenylalanine residue containing a free radical, which is available to crosslink with other amino acids and/or proteins within proximity.

"Detection" refers to detecting, observing, or measuring a construct on the basis of the properties of a detection label.

The term "labile" refers to a bond or bonds in a molecule with the potentiality of being cleaved by reagents, enzymes, or constituents of a cell.

The term "nucleobase-modified" refers to base-pairing derivatives of A, G, C, T, U, the naturally occurring nucleobases found in DNA and RNA.

A "membrane permeable construct" refers to a molecule comprised of two or more separately-identifiable moieties, wherein the moieties have been joined together to form a single moiety, or "construct," and wherein the entire construct is membrane-permeable. That is, the entire construct has the ability to cross a lipid or cell membrane.

A label is "incorporated into" a substrate moiety or a cell-penetrating peptide when the label is attached to, incorporated within, integrated into, or linked to the substrate moiety or the cell-penetrating peptide. This includes coupling of a label to the terminus of a substrate moiety or a cell-penetrating peptide as well as incorporating the label into a substrate moiety or a cell-penetrating peptide by including an amino acid analog that contains such a label.

By "modification" is meant any alteration of any polypeptide of the invention. Possible modifications include, but are not limited to, the addition of flanking sequences at the C-terminus or N-terminus; the removal of terminal sequences at the C-terminus or N-terminus; and/or the inclusion of nontraditional amino acid residues. Other modifications known in the art will be readily understood by the skilled artisan to be included herein.

"Variant" as the term is used herein, is a polypeptide sequence that differs in sequence from a reference polypeptide sequence, but retains essential properties of the reference molecule. One example of a retained essential property would be the ability of the variant to interact with the intracellular enzyme much like the reference polypeptide sequence. A variant of a polypeptide can be a naturally occurring such as an allelic variant, or can be a variant that is not known to occur naturally. Non-naturally occurring variants of polypeptide may be made by mutagenesis techniques or by direct synthesis. Preferably, the variant shares at least about 80% homology with the reference polypeptide sequence. More preferably, the variant shares at least about 90% homology with the reference polypeptide sequence. Even more preferably, the variant shares at least about 95% homology with the reference polypeptide sequence.

"Fragment" as the term is used herein, is a polypeptide sequence that differs in length (i.e., in the number of amino acids) from the length of a reference polypeptide sequence, but retains essential properties of the reference molecule. One example of a retained essential property would be the ability of the fragment polypeptide to interact with an intracellular enzyme much like the reference polypeptide sequence. A fragment of a polypeptide can be a naturally occurring or can be a fragment that is not known to occur naturally. Non-naturally occurring fragments may be made by mutagenesis techniques or by direct synthesis. Preferably, the fragment is at least about 25% of the length of the reference polypeptide sequence. More preferably, the fragment is at least about 35% of the length of the reference polypeptide sequence. Even more preferably, the fragment is at least about 45% of the length of the reference polypeptide sequence.

DESCRIPTION

I. Substrates and CPPs
A. Nucleic Acids Encoding a Cell-Penetrating Peptide

In one aspect, the present invention includes an isolated nucleic acid encoding a cell-penetrating peptide (CPP), or a functional fragment thereof, wherein the CPP comprises an amino acid sequence that confers cell-penetrating properties upon the CPP. As will be understood by one of skill in the art, a CPP has the ability to permeate a cell membrane, or be transported across a cell membrane. Further, as described elsewhere herein, a CPP has the ability to carry a cargo across a cell membrane. Such cargoes include, but are not limited to, a substrate, a peptide, a nucleic acid, an a photoreactive label. Other properties of CPPs include, but are not limited to, the ability to induce endocytosis of a cargo into a cell.

The CPP transportan has been shown to infiltrate the cell (Pooga, M., FASEB J., 12, 67-77 (1998)) and also to translocate proteins such as GFP and avidin-TRITC conjugate across the cell membrane as cargos (Pooga, M., et al., FASEB J., 10, 1096 (2001)). Additionally, transportan and its analogs have been used for transport of PNA antisense oligomers (Pooga, M., et al., Nat. Biotechnol., 16, 857-61 (1998)). Therefore, in one embodiment, a CPP of the invention is TP10, the sequence of which is set forth in SEQ ID NO:1. In another embodiment of the invention, the CPP is transportan, the sequence of which is set forth in SEQ ID NO:2. In another embodiment of the invention, a CPP is penetratin (RQIKIWFQNRRMKWKK; SEQ ID NO:3 (Derossi et al., 1994, J Biol Chem 269:10444-10450)). In yet another embodiment of the invention, a CPP is pTat (GRK-KRRQRRRPPQ; SEQ ID NO:4 (Vives et al., 1997, J Biol Chem 272:16010-16017)).

The skilled artisan, when armed with the disclosure set forth herein, will know how to identify a nucleic acid encoding a TP10 useful in the present invention. Briefly, a TP10 useful in the present invention is one that can form a membrane-permeable construct when coupled with a substrate moiety comprising at least one photoreactive moiety. That is, any TP10 that confers the property of membrane permeability upon a TP10-substrate-photoreactive moiety construct is encompassed by the present invention. Similarly, the skilled artisan will appreciate that a nucleic acid encoding any CPP that confers the property of membrane permeability upon a TP10-substrate-photoreactive moiety construct is also included in the present invention.

B. Polypeptide Substrates

The present invention features substrates that are a polypeptides. Substrates of the invention are generally synthesized using known synthetic techniques. High resolution and separation efficiency are challenging in the analysis and purification of molecules such as the substrates, polypeptides, and constructs of the invention, which may adopt multiple, stable conformations due to charges and intramolecular hydrogen-bonding. Under the non-denaturing, reverse-phase conditions used in a conventional HPLC separation, multiple peaks may be present, complicating product identification and collection.

Therefore, in one embodiment of the invention, SDS-polyacrylamide gel electrophoresis (SDS-PAGE) can be used for the analysis and purification of the substrates, polypeptides, and constructs of the invention. The skilled artisan will known how to isolate substrates, polypeptides, and constructs from an electrophoresis run by performing electrophoresis of the sample under standard conditions, excising the band after visualization under UV light or after staining with an appropriate stain, soaking in water overnight at room temperature, and desalting/concentrating. However, the present invention should not be limited to only such purification conditions as described herein. Rather, the skilled artisan, when armed with the present disclosure, will understand that other methods of isolation and purification are available. For protein isolation and purification methods known to the skilled artisan, see, for example: Davies and Chan, 2006, Amino Acids, Peptides and Proteins, Royal Society of Chemistry; Howl, 2005, Peptide Synthesis And Applications, Humana Press; Cutler, 2004, Protein Purification Protocols, Humana Press; Roe, 2001, Protein Purification Techniques: A Practical Approach, Oxford University Press; and Janson and Rydén, 1998, Protein Purification Principles, High-resolution Methods, and Applications, Wiley-VCH; all of which are incorporated by reference herein in their entirety.

C. Substrates with Photoreactive Labels

The present invention features a substrate moiety that includes at least one photoreactive label. That is, a substrate moiety of the invention comprises at least one photoreactive label. In one embodiment of the invention, a photoreactive label is a photoreactive amino acid. A photoreactive label of the present invention is useful for the crosslinking of a substrate moiety with an enzyme interacting with the substrate. In one embodiment of the invention, a photoreactive label is used to crosslink a polypeptide substrate moiety with an enzyme.

Examples of photoreactive labels useful for crosslinking according to the present invention include, but are not limited to, azido compounds, diazo compounds, and the like. When photoreactive labels are employed, typical crosslinking conditions comprise exposure to ultraviolet radiation at a temperature in the range of about 4° C. up to about 40° C. for a time in the range of about 0.1 minutes up to about 10 minutes, at a range of 0.1 to 100 inches from the label-containing sample. However, the invention should not be construed to be limited to these conditions, and the skilled artisan would understand, when armed with the disclosure set forth herein, that the crosslinking conditions can be varied according to the conditions and the needs for any particular set of circumstances.

By way of a non-limiting example, a photoreactive amino acid useful in the present invention includes, but is not limited to, para-benzoylphenylalanine (BPA) and paraazidophenylalanine. Other photoreactive labels useful in the present invention include, but should not be construed to be limited to, a benzoylbenzoyl (BzBz) moiety, an azide moiety, 4-benzoylbenzoic acid derivatives, 4-azido-2,3,5,6,-tetrafluorobenzoic acid derivatives, and N-((2-pyridyldithio)ethyl)-4-azidosalicylamide derivatives, and the like.

A photoreactive moiety may be incorporated into a substrate, as described in detail elsewhere herein. In one embodiment of the invention, a photoreactive moiety is chemically attached to a substrate moiety of the invention. In another embodiment, a photoreactive moiety is conjoined with a substrate moiety as part of an amino acid or polypeptide construct. For example, a photoreactive amino acid can be attached to a substrate moiety through ester-mediated coupling chemistry. Alternatively, a photoreactive amino acid can be attached to a substrate moiety through one or more amino acids to which the photoreactive amino acid is bonded. Based on the disclosure set forth herein, the skilled artisan would understand how to couple a photoreactive moiety to a substrate, using synthetic methods well-known in the art.

A photoreactive moiety may also be incorporated into a CPP, and the CPP consequently chemically coupled with a substrate, in order to incorporate the photoreactive moiety into a substrate. Methods of coupling a substrate moiety to a CPP are described in detail elsewhere herein. A photoreactive moiety may be incorporated into a CPP by coupling the photoreactive moiety to a terminus of the CPP, to a residue sidechain in the CPP, or to the backbone of the CPP. A photoreactive moiety may also be incorporated into a CPP by including the photoreactive moiety as part of a amino acid residue, or other subunit of the CPP, thereby making the photoreactive moiety an integral part of the CPP by way of incorporation of an amino acid residue, or other subunit, into the CPP structure.

A photoreactive moiety may also be incorporated into a linker moiety used to couple a substrate moiety with a CPP. In one embodiment, a photoreactive moiety is contained within a linker moiety used to couple a substrate moiety with a CPP. The photoreactive moiety may be internally located in the linker, or the photoreactive moiety may be at one terminus of the linker. In another embodiment, a photoreactive moiety is the linker moiety used to couple a substrate moiety with a CPP.

In all embodiments of the invention, it will be understood that more than one photoreactive moiety may be incorporated into a substrate, in any combination of locations within the substrate, CPP, or the linker coupling the CPP and substrate.

D. Other Nucleic Acids

The present invention should not be construed as being limited solely to the substrates, or to the nucleic acids encoding polypeptide substrates or polypeptide CPPs, as disclosed herein. Once armed with the present invention, it is readily apparent to one skilled in the art that other substrates, and other nucleic acids encoding other polypeptide substrates or other polypeptide CPPs, can be obtained by following the procedures described herein in the experimental details section for the generation of other nucleic acid and substrates as disclosed herein (e.g., site-directed mutagenesis, frame shift mutations, various chemical synthetic and modifying methods, and the like), and procedures that are well-known in the art or to be developed.

Further, any other number of procedures may be used for the generation of modified, derivative or variant forms of a substrate, or of a CPP, by using recombinant DNA methodology well known in the art such as, for example, that described in Sambrook et al. (2001, Molecular Cloning: A Laboratory Manual, Cold Spring Harbor Laboratory Press, New York) and Ausubel et al. (1997, Current Protocols in Molecular Biology, Green & Wiley, New York). Procedures for the introduction of amino acid changes in a protein or polypeptide by altering the DNA sequence encoding the polypeptide are well known in the art and are also described in Sambrook et al. (2001, supra); Ausubel et al. (1997, supra).

II. Polypeptides

The present invention includes an isolated CPP. As described in detail elsewhere herein, a CPP has the ability to permeate a cell membrane, or to be transported across a cell membrane, as well as the ability to carry a cargo across a cell membrane. In one aspect of the invention, the isolated polypeptide comprising a CPP is at least about 50% identical to a polypeptide having the amino acid sequence of SEQ ID NO:1 (AGYLLGKINLKALAALAKKIL), or a fragment thereof. Preferably, the isolated CPP is about 55% identical, more preferably, about 60% identical, more preferably, about 65% identical to SEQ ID NO:1, or some fragment thereof. Even more preferably, the isolated CPP is about 70% identical, more preferably, about 75% identical, more preferably, about 80% identical to SEQ ID NO:1, or some fragment thereof. More preferably, the isolated CPP is about 85% identical, more preferably, about 90% identical, more preferably, about 95% identical to SEQ ID NO:1, or some fragment thereof. Even more preferably, the isolated CPP is about 96% identical, more preferably, about 97% identical, more preferably, about 98% identical, and even more preferably about 99% identical to SEQ ID NO:1, or some fragment thereof. Most preferably, the portion of the isolated polypeptide comprising a CPP is SEQ ID NO:1, the amino acid sequence for TP10.

The skilled artisan, when armed with the disclosure set forth herein, will know how to identify a CPP useful in the present invention. Briefly, a CPP useful in the present invention is one that can form a membrane-permeable construct when coupled with a substrate moiety comprising at least one photoreactive moiety. That is, any CPP that confers the property of membrane permeability upon a CPP-substrate-photoreactive moiety construct is encompassed by the present invention.

In one embodiment of the invention, as CPP is TP10, the sequence of which is set forth in SEQ ID NO:1. In another embodiment of the invention, a CPP is penetratin (RQIKIWFQNRRMKWKK; SEQ ID NO:3 (Derossi et al., 1994, J Biol Chem 269:10444-10450)). In yet another embodiment of the invention, a CPP is pTat (GRKKRRQRRRPPQ; SEQ ID NO:4 (Vives et al., 1997, J Biol Chem 272:16010-16017). In general, all polypeptides that are referred to as CPPs or membrane translocating sequences or protein transduction domains are reviewed in (Eiriksdottir et al., 2004, Drug Delivery Reviews 1:161-173).

In still another embodiment of the invention, a CPP is transportan (Pooga, M., et al., FASEB J., 12:67-77 (1998)). Transportan may be synthesized in whole or in part, by one or more of the methods including biological protein expression and chemical polypeptide synthesis, as described in detail elsewhere herein. In another embodiment, transportan may be conjugated to a substrate, also as described elsewhere herein. The sequence of transportan is as follows:

(SEQ ID NO: 2)
GWTLNSAGYLLGKINLKALAALAKKIL-amide.

Transportan (galparan) is a 27 amino acid peptide from the N-terminus of the neuropeptide galanin (Bartfai, T., Raven Press, 1185 Ave of the Americas, New York, N.Y. 10036 (1995)); (Habert-Ortoli, E., et al., Proc. Natl. Acad. Sci. USA, 91:9780-83 (1994)), and mastoparan in the C-terminus, both fragments connected via a lysine. Transportan is a cell-penetrating peptide as judged by indirect immunofluorescence using the biotinylated analog, Nδ13-biotinyl-transportan. The uptake of transportan is rapid and efficient, and the internalization of biotinyl-transportan is energy independent and efficiently takes place from 0-37° C. and the maximal intracellular contraction is reached in about 20 min at 37° C. The cell-penetrating ability of transportan is not restricted by cell type, but is a general feature of the peptide sequence (for example, see Langel et al., U.S. Pat. No. 6,025,140).

However, a CPP useful in the present invention should not be limited to those disclosed herein. Rather, the skilled artisan, when armed with the present disclosure, will understand that any CPP that can transport a substrate moiety into a cell, known now or yet to be discovered, should be construed to be encompassed by the present invention. The present invention also provides for analogs of proteins or polypeptides which comprise a CPP as disclosed herein. Analogs may differ from naturally occurring proteins or polypeptides by conservative amino acid sequence differences or by modifications which do not affect sequence, or by both. For example, conservative amino acid changes may be made, which although they alter the primary sequence of the protein or polypeptide, do not normally alter its function. Conservative amino acid substitutions typically include substitutions within the following groups:
  glycine, alanine;
  valine, isoleucine, leucine;
  aspartic acid, glutamic acid;
  asparagine, glutamine;
  serine, threonine;
  lysine, arginine;
  phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are substrate moieties and CPPs which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "derivatives," and "variants" of the peptides of the invention (or of the DNA encoding the same) which derivatives and variants are a CPP which has been altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of a CPP of the present invention. For example, a variant of the CPP transportan may have one or more additional amino acids added to either end of the peptide. Such biological/biochemical properties include, but are not limited to, the transport of a cargo across a cell membrane.

The present invention also includes substrate moieties and CPPs to which one or more labels have been added. A label may be used for the identification and/or purification of the peptide, or for the identification of the biological role or biological interactions of the peptide. A label useful in the present invention should have a unique or identifiable property, such as fluorescence, radioactive signal, light emission, phosphorescence, paramagnetism, and the like, which may be detectable using any spectroscopic or spectrophotometric technique known in the art. Protein labels useful in the present invention includes, but should not be limited to, biotin, dinitrophenyl, acridine, fluorescein, rhodamine, cyanine (such as Cy3 and Cy5, among others), digoxigenin, a chemiluminescent precursor, selenium, cadmium, labels useful in quantum dot technology, and known-antibody epitopes (such as c-myc, among others) and the like.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The peptides of the present invention may be readily prepared by standard, well-established solid-phase peptide synthesis (SPPS) as described by Stewart et al. (Solid Phase Peptide Synthesis, 2nd Edition, 1984, Pierce Chemical Company, Rockford, Ill.) and as described by Bodanszky and Bodanszky (The Practice of Peptide Synthesis, 1984, Springer-Verlag, New York). At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method which utilizes tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF (hydrofluoric acid) treatment releases a peptide bearing an N-methylamidated C-terminus. Blockage of the C-terminus by esterification can also be achieved using conventional procedures. This entails use of resin/ blocking group combination that permits release of sidechain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequencers, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies or for specific uses. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

III. Membrane-Permeable Constructs

The present invention further includes an isolated peptide construct comprising a CPP and a substrate moiety. One portion of a construct of the invention comprises a cell-penetrating peptide (CPP). Another portion of the present invention includes a substrate moiety, which further comprises a photoreactive moiety. The substrate moiety comprises a peptide sequence which is a substrate moiety of an enzyme. The utility of the construct of the invention is that the CPP can carry a cargo, such as a substrate moiety, across a cell membrane and into a cell.

After transport of the construct across a cell membrane, and upon binding of the substrate moiety portion of the construct to an intracellular enzyme, the photoreactive moiety of the substrate moiety is in close proximity to the enzyme that is also bound to the substrate. Upon activation of the photoreactive moiety on the substrate, the activated moiety can chemically crosslink to the enzyme. Specific separation of the enzyme crosslinked complex can then facilitate identification of the enzyme.

In one embodiment of the invention, the CPP transportan is used for intracellular delivery of a substrate. A photoreactive amino acid adduct, p-benzyolphenylalanine (BPA), is attached to the substrate, and the substrate-BPA conjugate is attached to the transportan by way of a disulfide linkage. Following transport of the substrate moiety across a cell membrane by transportan, the substrate moiety interacts with the enzyme. UV irradiation of the construct-containing cell activates the BPA, causing the benzyol moiety of the BPA to be released, and creating a free phenylalanine radical that can crosslink the nearest substances, i.e. the enzyme bound to the substrate. The crosslinked complex is then isolated by methods known in the art and elsewhere described herein.

In this way, in-vivo enzyme capture ("IVEC") according to the present invention provides an in vivo methodology through which an enzyme that interacts with any substrate moiety can be identified. The general conjugation strategy to prepare a construct of the invention is to synthesize the substrate moiety and the CPP moieties separately. Reagents and automated synthesizers are commercially available for the synthesis of peptides. Each moiety can be further derivatized to contain reactive functionality to form a linkage. Substrates can be covalently coupled to peptides through any suitable bond. In one embodiment of the invention, suitable bonds include labile bonds, such as a disulfide. To form a disulfide bond in a construct between the substrate moiety and peptide, the two moieties may be derivatized to contain thiol groups, one of which can contain a leaving group. In another embodiment of the invention, a linkage may be formed between a substrate moiety and a CPP using avidin-biotin chemistry. Methods of coupling avidin and biotin to a substrate moiety and a CPP are well-known in the art and will not be discussed herein.

Labile linkers allow degradation of the CPP-substrate moiety construct, which may be important under some conditions for reduction of unwanted effects, or for optimization of the function of the substrate. For intracellular delivery, various labile linkers can be used. By way of a non-limiting example, disulfide bridges, pH sensitive linkers and protease/nuclease substrates can be used. The intracellular milieu is highly reducive in chemical potential, due to high (mM range) concentration of glutathione. Thiol-containing gluthathione can exist in oxidized (disulfide) or reduced (thiol) form, the ratio of which is regulated by the enzyme glutathione-S-transferase, as well as other oxidative species. Compounds containing a disulfide bond undergo reaction with reduced gluthatione, leading to a reduced disulfide bond and oxidized gluthatione. For disulfide-containing CPP conjugates, the process has been characterized by Hallbrink et al. (2001, Biochim Biophys Acta. 1515:101-9).

Such constructs can cross the membrane directly over the cell membrane, or in other cases, by endocytosis. Endocytotic uptake mechanisms involve a pH drop in endocytotic vesicles after internalization. Therefore, in one embodiment of the invention, pH sensitive linkers are utilized for enhanced release of the substrate moiety from the CPP upon pH change. Linkers useful for this purpose include cyclic, unsaturated maleamates, and 13-acylhydrazone, among others (Fletcher et al., 2004, Org. Lett. 6:4245-4248; Braslawsky et al., 1991, Cancer Immunol Immunother. 33:367-74). In another embodiment of the invention, enzymes, such as penicillin G acylase, can be utilized to mediate separation of a CPP from a substrate. (Grether et al., 2001, Chemistry 7:959-971.)

In another embodiment of the invention, substrate moiety internalization into a cell is enhanced by attachment of a moiety to a substrate moiety that drives internalization. Such moieties include, but should not be limited to, $(Lys)_{1-4}$, CPP, a ligand which is internalized, a peptide or ligand attached to a substrate moiety by way of a disulfide bond, a nuclear localization signal, a highly positively charged heptamer, such as PKKKRKV from the SV40 core protein. In one embodiment of the invention, $[N_{13\epsilon}$-Cys(Npys)]-Transportan is the attached moiety.

In an embodiment of the invention, a scheme for conjugation, or coupling, of the substrate moiety and CPP moieties set forth herein, includes a substrate moiety derivatized with a nitropyridyl-leaving group (Npys) on a cysteine amino acid, as described in greater detail in the Experimental Examples. Displacement by the substrate moiety thiol of the Npys group of the peptide yields the disulfide-linked construct.

Therefore, the skilled artisan would understand, when armed with the disclosure set forth herein for the first time, that the present invention is useful to identify the mechanisms involved in the onset and progression of any imbalance, disease or condition that is influenced by or regulated by enzymes. The present invention therefore provides a powerful new tool for understanding and using fundamental molecular biology in order to develop novel therapeutics.

The skilled artisan will also understand that the constructs and methods described herein can be used with the cells from any living species. That is because the invention enables an improved, more efficient drug discovery, aids in identifying novel points of therapeutic intervention, and provides a generalized method for the introduction of a substrate moiety into essentially any cell by way of the membrane permeant activity of the CPP constructs of the invention.

IV. Vectors

In other related aspects, the invention includes an isolated nucleic acid encoding a substrate moiety and/or a CPP operably linked to a nucleic acid comprising a promoter/regulatory sequence such that the nucleic acid is preferably capable of directing expression of the substrate moiety encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Expression of a CPP, either alone or fused to a detectable tag polypeptide (e.g. c-myc Ab epitope), or fused to a substrate, in a cell can be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, as well as the Rous sarcoma virus promoter and the like. Moreover, inducible and tissue specific expression of the nucleic acid encoding a CPP may be accomplished by placing the nucleic acid encoding a CPP, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, hormones, and the like, are also contemplated in the invention. Thus, it will be appreciated that the invention includes the use of any promoter/regulatory sequence, which is either known or unknown, and which is capable of driving expression of the desired protein operably linked thereto.

Expressing a CPP using a vector allows the isolation of large amounts of recombinantly produced protein. Further, expression of a CPP driven by a promoter/regulatory sequence can allow expression of a CPP in various cell and tissue types. Therefore, the invention includes not only methods of producing a CPP for use in the methods of the present invention, the present invention further includes methods of expression a CPP in any cell or tissue type known in the art, including eukaryotic cells, prokaryotic cells, tissue samples from eukaryotic organisms, and the like.

Selection of any particular plasmid vector or other DNA vector is not a limiting factor in this invention and a wide variety of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The invention thus includes a vector comprising an isolated nucleic acid encoding a CPP. The incorporation of a desired nucleic acid into a vector and the choice of vectors is well-known in the art as described in, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The invention also includes cells, viruses, proviruses, and the like, containing such vectors. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a CPP may be cloned into various plasmid vectors. However, the present invention should not be construed to be limited to plasmids or to any particular vector. Instead, the present invention should be construed to encompass a wide plethora of vectors which are readily available and/or well-known in the art.

V. Recombinant Cells

The invention includes a recombinant cell comprising, inter alia, an isolated nucleic acid encoding a CPP, a nucleic acid encoding an antibody that specifically binds a CPP, a nucleic acid encoding an substrate, and combinations thereof. In one aspect, the recombinant cell can be transiently transfected with a plasmid encoding a portion of the nucleic acid. The nucleic acid need not be integrated into the cell genome nor does it need to be expressed in the cell.

Moreover, the cell may be a prokaryotic or a eukaryotic cell and the invention should not be construed to be limited to any particular cell line or cell type. Such cells include, but are not limited to, E. coli, insect cells, yeast cells, and mammalian cells.

VI. Antibodies

The present invention further includes an antibody that specifically binds a CPP moiety, a substrate moiety, a CPP-substrate construct, or an optional known-antibody epitope, of the present invention, or fragments, variants or modifications thereof.

One skilled in the art would understand, based upon the disclosure provided herein, that an antibody that specifically binds CPP, a substrate, a CPP-substrate construct, or an optional known-antibody epitope, is useful for, inter alia, the detection of such molecules in a cell, tissue or organ. The antibody can also be used to isolate and/or purify CPP, a substrate, or a CPP-substrate moiety construct. Further, once a CPP-substrate construct has been crosslinked to an enzyme by way of a photoactivatable moiety contained within the construct, an antibody can be used to isolate and/or purify the crosslinked complex.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the CPP, substrate, or a CPP-substrate construct portion is rendered immunogenic (e.g., CPP conjugated with keyhole limpet hemocyanin, KLH). The chimeric proteins are produced by cloning the appropriate nucleic acids encoding, for example, CPP, a substrate, or a CPP-substrate moiety analog construct (e.g., SEQ ID NO:1) into a plasmid vector suitable for this purpose, such as but not limited to, pMAL-2 or pCMX.

However, the invention should not be construed as being limited solely to polyclonal antibodies that bind a CPP, a substrate, or a CPP-substrate moiety analog construct. Rather, the present invention should be construed to encompass antibodies that, among other things, bind to a CPP, a substrate, a CPP-substrate moiety construct, or an optional known-antibody epitope, and are able to bind these molecule when present on Western blots or in cell lysates.

One skilled in the art would appreciate, based upon the disclosure provided herein, that the antibody can specifically bind with any portion of the protein and the full-length protein can be used to generate antibodies specific therefor. However, the present invention is not limited to using the full-length molecule as an immunogen. Rather, the present invention includes using an immunogenic portion of the molecule to produce an antibody that specifically binds with a CPP, a substrate, a CPP-substrate construct, or an optional known-antibody epitope. That is, the invention includes immunizing an animal using an immunogenic portion, or antigenic determinant, of CPP, a substrate, or a CPP-substrate moiety analog construct.

The antibodies can be produced by immunizing an animal such as, but not limited to, a rabbit or a mouse, with CPP, a substrate, a CPP-substrate construct, or an optional known-antibody epitope, or a portion thereof, or by immunizing an animal using a protein comprising at least a portion of a CPP, a substrate, or a CPP-substrate construct or a fusion protein including a tag polypeptide portion comprising, for example, a maltose binding protein tag polypeptide portion, covalently linked with a portion comprising the appropriate CPP, a substrate, or a CPP-substrate moiety construct. The skilled artisan can also use smaller fragments of these proteins to produce antibodies that specifically bind CPP, a substrate, or a CPP-substrate moiety construct.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein.

Further, the antibody of the invention may be "humanized" using the technology described in, for example, Wright et al. (1992, Critical Rev. Immunol. 12:125-168), and in the references cited therein, and in Gu et al. (1997, Thrombosis and Hematocyst 77: 755-759). The present invention also includes the use of humanized antibodies specifically reactive with epitopes of a CPP, a substrate, or a CPP-substrate moiety construct. Such antibodies are capable of specifically binding a CPP, a substrate, or a CPP-substrate moiety construct, or a fragment thereof. The humanized antibodies of the invention have a human framework and have one or more complementarity determining regions (CDRs) from an antibody, typically, but not limited to a mouse antibody, specifically reactive with a CPP, a substrate, or a CPP-substrate moiety construct, or a fragment thereof.

When the antibody used in the invention is humanized, the antibody may be generated as described in Queen, et al. (U.S. Pat. No. 6,180,370), Wright et al., (1992, Critical Rev. Immunol. 12:125-168) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as a CPP, a substrate, or a CPP-substrate moiety construct, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well known procedures. Preferably, the human constant region DNA sequences are isolated from immortalized B-cells as described in WO 87/02671, which is herein incorporated by reference. CDRs useful in producing the antibodies of the present invention may be similarly derived from DNA encoding monoclonal antibodies capable of binding to a CPP, a substrate, or a CPP-substrate moiety construct. Such humanized antibodies may be generated using well known methods in any convenient mammalian source capable of producing antibodies, including, but not limited to, mice, rats, rabbits, or other vertebrates. Suitable cells for constant region and framework DNA sequences and host cells in which the antibodies are expressed and secreted, can be obtained from a number of sources, for example, American Type Culture Collection, Manassas, Va.

In addition to the humanized antibodies discussed above, other modifications to native antibody sequences can be readily designed and manufactured utilizing various recombinant DNA techniques well known to those skilled in the art. Moreover, a variety of different human framework regions may be used singly or in combination as a basis for humanizing antibodies directed to a CPP, a substrate, or a CPP-substrate moiety construct. In general, modifications of genes may be readily accomplished using a variety of well-known techniques, such as site-directed mutagenesis (Gillman and Smith, Gene, 8:81-97 (1979); Roberts et al., 1987, Nature, 328:731-734).

Alternatively, a phage antibody library may be generated. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory, New York).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (1992, Critical Rev. Immunol. 12:125-168).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

VII. Methods

The present invention is based, in part, on the novel discovery that a CPP-substrate membrane permeable construct can be used to identify enzymes that bind to a substrate. As described in detail elsewhere herein, a CPP-substrate construct that contains one or more photoreactive groups can be used to crosslink a enzyme that interacts with the substrate moiety.

In one embodiment of the invention, a method is provided to identify a enzyme that interacts with a substrate. In one embodiment, a method of identifying a enzyme that interacts with a substrate moiety includes the steps of providing a membrane permeable construct to a cell under conditions suitable to allow the construct to cross the cell membrane, allowing the construct to bind with the intracellular enzyme to form a construct-substrate moiety complex, under conditions suitable for binding of the construct with the enzyme, activating a photoreactive moiety on the construct, thereby covalently cross-linking the substrate moiety with an enzyme that interacts with the substrate, isolating the crosslinked CPP-substrate-enzyme complex from the cell, and identifying the crosslinked enzyme.

In one aspect of the invention, the membrane-permeable construct includes a substrate moiety which contains at least one photoreactive amino acid. In one aspect, the photoreactive amino acid is BPA. In another aspect of the invention, the membrane-permeable construct includes a peptide moiety of the identity $R_1$-CPP-$R_2$, wherein CPP is a cell-penetrating peptide, further wherein each of $R_1$ and $R_2$ are independently selected from the group consisting of a peptide, an amino acid, $NH_2$, H, or OH, further wherein the substrate moiety is covalently attached to one of the members selected from the group consisting of $R_1$, $R_2$, a cysteine residue within said peptide moiety, or a lysine (K) residue within said peptide moiety. In another aspect of the invention, the CPP is transportan. In yet another aspect of the invention, the CPP is TP10, $R_1$-AGYLLGKINLKA-LAALAKKIL-$R_2$ (SEQ ID NO:1), wherein $R_1$ is hydrogen and $R_2$ is $NH_2$. Other CPPs useful in the present invention are described in detail elsewhere herein.

In an aspect of the invention, the substrate moiety is linked to the CPP moiety through a chemical bond. In one aspect, the bond is a disulfide bond. In still another aspect, a substrate moiety is covalently attached to a cysteine residue within the CPP moiety. Numerous other membrane permeable constructs useful in a method of the present invention are described in greater detail elsewhere herein, and will therefore not be discussed further at this point.

In another embodiment of the invention, a method of identifying a enzyme that interacts with an intracellular enzyme includes particular method steps for isolation of the crosslinked substrate-enzyme complex. In one aspect, the method includes lysing the cell containing the crosslinked substrate-enzyme to form a cell lysate and subjecting the lysate to a method employed for separating and identifying proteins, such as for example, SDS-PAGE, Immunoprecipitation and/or Western Blotting. See for example: Sambrook et al. (2001, Molecular Cloning: A Laboratory Manual, Cold Spring Harbor Laboratory Press, New York) and Ausubel et al. (1997, Current Protocols in Molecular Biology, Green & Wiley, New York). In yet another embodiment of the invention, the method includes lysing the cell containing the crosslinked substrate-enzyme to form a cell lysate, contacting the cell lysate with a solid support comprising an antibody specific for at least one of the CPP moiety, the substrate moiety, the CPP-substrate construct, or an optional known-antibody epitope. The incubation is conducted under conditions suitable to allow the crosslinked substrate-enzyme to bind to the antibody to form a complex, and separating the antibody complex from the cell lysate.

As will be understood by the skilled artisan, a method of the present invention is also amenable to the use of any solid support, based on the disclosure set forth herein, for isolation or purification of a substrate-enzyme complex.

VIII. Kits

The present invention encompasses various kits for identification of a enzyme that interacts with an substrate, comprising a CPP-substrate moiety membrane permeable construct, an applicator, and instructional materials which describe use of the kit to perform the methods of the invention. These instructions simply embody the methods and examples provided herein. Although model kits are described below, the contents of other useful kits will be apparent to the skilled artisan in light of the present disclosure. Each of these kits is contemplated within the present invention.

The membrane permeable construct of a kit of the invention includes a CPP portion linked to a substrate moiety portion. In one embodiment, the CPP portion is transportan. The construct further includes a substrate moiety portion. The construct further includes a photoreactive label. In one embodiment of the invention, the photoreactive label is a photoreactive amino acid. In one aspect, the photoreactive amino acid is part of the substrate moiety portion of the construct.

The membrane-permeable construct included in a kit of the present invention can be an isolated polypeptide as described elsewhere herein. Further, it will be understood that the compositions and the methods of the invention described herein are equally applicable to use in a kit of the invention.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Experimental Example 1

CPP-Substrate Construct

The CPP, TP10, was synthesized on an Applied Biosystems 431A synthesizer using t-Boc strategy and dicyclohexylcarbodiimide (DCC)/Hobt activation. The orthogonal protection group of (Pooga M., et al., Methods Mol. Biol., 208:225-36 (2002)) Lys was specifically removed after completion of main peptide chain and TBTU/Hobt activated t-Boc-Cys(Npys)-OH was coupled to the side chain. The substrate moiety is synthesized on an Applied Biosystems 431A synthesizer using t-Boc strategy and dicyclohexylcarbodiimide (DCC)/Hobt activation. The orthogonal protection group of (Pooga M., et al., Methods Mol. Biol., 208: 225-36 (2002)) Lys is specifically removed after completion of main peptide chain and TBTU/Hobt activated t-Boc-Cys(Npys)-OH is coupled to the side chain.

The CPP was cleaved from resin by hydrogen fluoride at 0° C., 45 min. p-cresol was used as scavenger. Cleaved CPP was purified on a reverse-phase HPLC($C_{18}$, Discovery 25 cm×21.2 mm, 5 µm, Supelco). The mass of the peptide was verified by MALDI-TOF (Voyager-DE STR) mass spectrometry. The substrate moiety is cleaved from resin by hydrogen fluoride at 0° C., 45 min. p-cresol was used as scavenger. Cleaved substrate moiety is purified on a reverse-phase HPLC($C_{18}$, Discovery 25 cm×21.2 mm, 5 µm, Supelco). The mass of the substrate moiety is verified by MALDI-TOF (Voyager-DE STR) mass spectrometry. 1 µmol of CPP and substrate moiety is conjugated in 100 µl dimethylsulfoxide (DMSO), 100 µl dimethylformamide and 300 µl 0.1 M acetic buffer pH 5.5. 30 µl trifluoroacetic acid is added in cases when it remains in pellet. The mixture is stirred at room temperature overnight and reaction products are separated on a reverse-phase HPLC $C_{18}$ column (Discovery, 25 cm×10 mm, 5 µm). The identity of each conjugate is determined by absorbance profile in a multiwavelength detector of the HPLC and MALDI-TOF mass spectrometry.

As illustrated below, a disulfide bridge is formed between the N-terminal Cys of the substrate moiety and the Cys coupled to the side chain of $Lys^7$ in TP10:

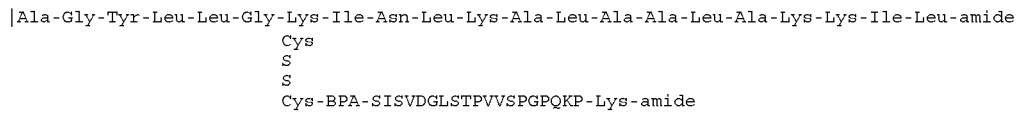

The peptide sequence substrate described in this example, which is serving as the substrate moiety of this example construct, is centered around the T417 phosphorylation site for the identification of putative T417 Elk-1 kinases. One of skill in the art will understand that any peptide sequence identified as, or suspected to be, a putative site of interaction with a known, or as yet unknown, enzyme, including, for example, the regions around a suspected, or known, post-translational or chemical modification site (such as for example a phosphorylation site) or other feature associated with an enzyme-substrate interaction site, can serve as the substrate moiety of the construct of the invention.

Experimental Example 2

Cell Culture

Cell cultures are maintained in a supplemented MEM or Neurobasal media at 37° C. in 5% $CO_2$. When the cells are of the appropriate age, they are either immediately put through the IVEC procedure or are pre-treated with pharmacological agonists or antagonists that activate relevant enzymatic pathways or allow for empirical screening of putative pathways. Following stimulation, the media is removed and the cells are washed with HBSS.

Experimental Example 3

IVEC Procedure

TP10-substrate moiety conjugates were suspended in 1M HBS (HEPES-buffered saline), pH 7.4 at a concentration of 5 μM and stored at −20° C. until used. Cells were incubated in culture with media, along with 50 nM TP10-substrate moiety diluted in pre-warmed media, for 90 minutes at 37° C. in 5% $CO_2$. The media containing the TP10-substrate moiety is aspirated from the culture dish, and ice cold 1M HBS, pH 7.4, are quickly added to the dish to wash the cells and prepare them for lysis. Prior to lysis, the cells are UV irradiated for 2.5 minutes at a distance of 2.5 inches from the UV source in order to crosslink the TP10-substrate moiety and the enzyme. The cells are then lysed.

Experimental Example 4

Cell Lysis and Isolation of Protein Lysate

The cells are lysed by removing the HBS after UV irradiation and quickly adding ice cold TX-100 lysis buffer containing freshly added protease inhibitors (25 mM HEPES, pH 7.4, 0.1% Triton X-100, 300 mM NaCl, 20 mM β-glycerophosphate, 1.5 mM $MgCl_2$, 1 mM DTT, 200 nM $Na_3VO_4$, 2 mM EDTA, pH 8.0, 1 mM benzamidine, 1 mM PMSF, 2 μg/ml leupeptin, 2 μg/ml aprotinin). The cells are immediately scraped off of the plate, collected, and put on ice. Protein lysate was stored at −80° C. for at least one hour until used, for example, for SDS-PAGE, Western Blotting and/or Immunoprecipitation.

Experimental Example 5

Enrichment and Isolation of Captured Enzyme from Total Protein Lysate

After thawing the lysate on ice, pre-clear the cell lysate with Sepharose beads (such as, for example, protein G-coupled Sepharose beads, or protein A-coupled Sepharose beads, depending on the type of antibody employed) for 1-3 hours at 4° C. to remove non-specific interactions with the beads. Subsequently, spin down the lysate at 4° C. to remove the beads as well as the insoluble membrane fraction. Remove the supernatant and add the manufacturer-recommended amount of antibody, such as anti-c-myc (i.e., EQKLISEEDL; SEQ ID NO: 5) antibody. One skilled in the art will understand that the amount of lysate and antibody used will be chosen depending on the concentration and amount of the protein and the affinity of the antibody for the protein. The lysate is then incubated with the antibody between 1 hour to overnight, as necessary, at 4° C., preferably with gentle agitation. Prepare Sepharose beads by washing 100 mg of beads in 1 ml of 0.1 M PBS three times, or as necessary. The beads are then incubated with the lysate at 4° C. for 4 hours. After 4 hours, centrifuge the tubes, remove the supernatant and wash the beads in lysis buffer three times. Remove the final wash and add 25-50 ul of 2× loading buffer. Boil at 95-100° C. for 5 minutes to denature the protein, cool on ice and spin down to separate it from the Sepharose beads. The Immunoprecipitates can now be frozen at −80° C. or used to conduct, for example, SDS-PAGE and/or Western Blot analysis, and the like.

Experimental Example 6

Gel Electrophoresis and Staining

SDS-PAGE can be performed on the total lysate and/or the Immunoprecipted crosslinked enzyme complexes. To examine the results obtained using the IVEC protocol, the Biorad Silverstain Plus Kit (Biorad Cat. No. 161-0449) is used to visualize the protein. Once the optimal conditions are determined using the more sensitive silver stain, visualization of bound enzyme is carried out using coomassie blue protein staining prior to mass spectometry. Protein gels are incubated at room temperature, with shaking, in a fixative (46% methanol, 7% acetic acid) for one hour, followed by one hour in stain (46% methanol, 7% acetic acid, filter-sterilized 0.1% Coomassie Stain Brilliant Blue R-250), and then were de-stained in 5% methanol, 7.5% acetic acid until protein bands could be detected. At that point, the gels are transferred into a 5% acetic acid stop solution. Bands are then extracted from the gel, and the gel slices are put into 1-2% acetic acid and stored at −20° C. until mass spectrometry was performed.

Experimental Example 7

Conjugation of Substrate Moiety to a CPP Using a Disulfide Bond

To obtain heterodimeric disulfide bridge between a substrate moiety and a cell penetrating peptide, the cysteine residue of one component, either substrate moiety or peptide, must be derivatized. 3-Nitro-2-pyridinesulphenyl (NPys)-derivatised Cys is specifically reactive towards free thiols. Npys labelled Cys is commercially available and can be assembled into peptide chain like a commonly protected amino acid.

First, 1 molar equivalent (0.5-2 mg) of peptide and 1 molar equivalent of substrate moiety is prepared in separate microcentrifuge tubes. The coupling efficiency varies between sequences of both substrate moiety and peptide, and depends on solubility and purity of each. Therefore, a 1:1 molar ratio may not be optimal in every case, and optimization of the ratio will be required to achieve the desired results. Substrate moiety is dissolved in 200 µl deoxygenated DMSO. Peptide is dissolved in 100 µl of 0.01 M acetic buffer pH 5.5, and 200 µl of DMF is added to both of the solutions. The two solutions are mixed and vortexed thoroughly. The mixture is stirred overnight, or at least for 4 hours, at room temperature, shielded from light.

Reaction products can be separated by semipreparative RP-HPLC. A C-18 column, or the column used for purification of the peptide, if different, is used. An isocratic gradient can be used, for example, 20% eluent A for 5 min, followed by gradual increase of eluent A to 100% in 40 min. 20% acetonitrile will prevent "unreacted" substrate moiety from interacting with the stationary phase in the column, and unreacted substrate moiety will be washed out of the column together with solvents (DMSO and DMF). Detection wavelengths used include 218 nm (absorbance maximum for peptide bond). For single wavelength detector, 260 nm is used for detection. Fractions absorbing both wavelengths are collected.

Fraction(s) are freeze-dried and stored in the dark at −20° C. Mass spectrometry analysis of the conjugate may be used to further verify the desired product. Care must be taken as not to reduce the disulfide bridge during preparation of a sample or collection of mass spectrometric data.

Experimental Example 8

Phosphatase Capture

Figure 4:
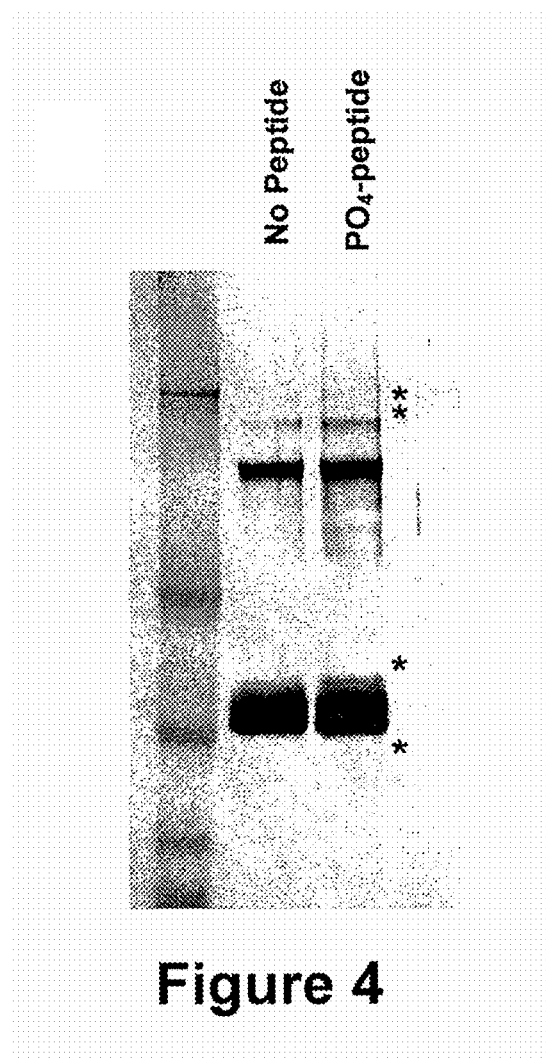
FIG. 4 depicts an exemplary capture of a phosphatase targeting a phosphorylated peptide. The asterisks correspond to protein IDs that are present in the peptide containing sample lane relative to the no peptide control, and hence are phosphatase candidates. Differences in banding patterns and intensity are depicted in FIG. 4.

In an effort to identify phosphatases that would function on phosphorylated-Elk1, a PAIR-peptide corresponding to the T417 was used, where the phosphorylation site was actually phosphorylated. The in vivo proteins that bind to this peptide are likely to be enriched for those proteins that recognize this amino acid sequence when it is phosphorylated, with the strongest candidates being phosphatases. As depicted in FIG. 4, the asterisks correspond to protein IDs that are present in the peptide containing sample lane relative to the no peptide control, and hence are phosphatase candidates. The sequence, and therefore identity, of these proteins can be determined by mass spec analysis.

Two week old hippocampal neurons from primary culture were treated briefly with 0.1% fatty-acid free BSA and then washed with normal rat saline. A synthetic peptide was then added to the cells and incubated 5 minutes at room temperature to load the cells. This peptide contains the amino acid sequence for the phosphorylated T417 epitope sequence of Elk-1 attached to the photoactivatable compound p-Benzoyl-phenylalanine, a cell penetrating peptide M918, and the epitope tag for c-myc. The cells were then briefly washed again with saline and then stimulated with 100 nm glutamate for 1 minute. Crosslinking was performed for 5 minutes by exposing cells to UVA and UVB for 5 minutes. Cells were then lysed in ice cold lysis buffer containing phosphatase inhibitors and frozen at −80° C. for 1 hour. Immunoprecipitation was performed using a Dynabeads Protein G(Invitrogen) kit using an antibody to the c-myc epitope tag (Abeam). Samples were run out on a 7% Tris-acetate gel and silver stained using a SilverQuest kit (Invitrogen). Bands can then be isolated and kinases and phosphatases identified using gas-chromatography-mass spectrometry. Differences in banding patterns and intensity are depicted in FIG. 4.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of identifying an enzyme that interacts with a substrate, said method comprising the steps of:
   a) providing a polypeptide molecule comprising:
      i) a substrate moiety which interacts with an intracellular enzyme, said substrate moiety comprising a peptide and at least one photoreactive crosslinking moiety;
      ii) a peptide moiety comprising R1-CPP-R2, wherein CPP is a cell-penetrating peptide, further wherein each of R1 and R2 are independently selected from the group consisting of a peptide, an amino acid, NH2, H, or OH, further wherein said substrate moiety is covalently attached to one of the members selected from the group consisting of R1, R2, a cysteine residue within said peptide moiety, or a lysine (K) residue within said peptide moiety; and
      iii) a chemical bond linking said substrate moiety and said peptide moiety;
   b) allowing said molecule to interact with said intracellular enzyme in a cell to form a molecule-enzyme complex, under conditions suitable for binding of said molecule with said enzyme;
   c) activating said photoreactive crosslinking moiety, thereby covalently cross-linking said substrate moiety with said enzyme that interacts with said substrate;
   d) isolating said crosslinked substrate-enzyme from said cell; and
   e) identifying said enzyme crosslinked to said substrate; thereby identifying an enzyme that interacts with a substrate.

2. The method of claim 1, wherein said isolating step d) comprises:
   i) lysing the cell containing the crosslinked substrate-enzyme to form a cell lysate;
   ii) contacting said cell lysate with a solid support comprising an antibody specific for at least one of the members of the group consisting of:
      A) the CPP;
      B) the substrate moiety; and
      C) the polypeptide molecule under conditions suitable to allow said crosslinked substrate-enzyme to bind to said antibody to form a complex; and
   iii) separating said complex from said lysate.

* * * * *